(12) United States Patent
Domb et al.

(10) Patent No.: US 9,161,909 B2
(45) Date of Patent: Oct. 20, 2015

(54) ADHESIVE COMPOSITIONS FOR THE TREATMENT OF XEROSTOMIA

(75) Inventors: Abraham J. Domb, Efrat (IL); Benny Brama, Raanana (IL); Boaz Mizrahi, Brookline, MA (US)

(73) Assignee: Axiomedic Ltd., Gibraltar (GI)

( * ) Notice: Subject to any disclaimer, the term of this patent is extended or adjusted under 35 U.S.C. 154(b) by 366 days.

(21) Appl. No.: 12/757,508

(22) Filed: Apr. 9, 2010

(65) Prior Publication Data

US 2010/0247644 A1 Sep. 30, 2010

Related U.S. Application Data

(63) Continuation-in-part of application No. 11/959,997, filed on Dec. 19, 2007, now abandoned.

(60) Provisional application No. 60/957,899, filed on Aug. 24, 2007.

(51) Int. Cl.
  *A61K 9/20* (2006.01)
  *A61K 9/00* (2006.01)
  *A61K 31/22* (2006.01)

(52) U.S. Cl.
  CPC .............. *A61K 9/006* (2013.01); *A61K 9/2086* (2013.01); *A61K 31/22* (2013.01)

(58) Field of Classification Search
  None
  See application file for complete search history.

(56) References Cited

U.S. PATENT DOCUMENTS

| | | | |
|---|---|---|---|
| 4,276,287 A | 6/1981 | Cabardo, Jr. | |
| 4,615,697 A | 10/1986 | Robinson | |
| 5,580,880 A | 12/1996 | Handa et al. | |
| 5,686,094 A | 11/1997 | Acharya | |
| 5,804,165 A | 9/1998 | Arnold | |
| 5,817,294 A | 10/1998 | Arnold | |
| 5,962,503 A | 10/1999 | Ekstrom et al. | |
| 5,965,110 A | 10/1999 | Arnold | |
| 6,063,404 A * | 5/2000 | Timpe et al. | 424/464 |
| 6,086,854 A | 7/2000 | Arnold | |
| 6,325,991 B1 | 12/2001 | Draheim | |
| 6,458,777 B1 | 10/2002 | Sonis | |
| 7,198,779 B2 | 4/2007 | Rifa Pinol et al. | |
| 2004/0156794 A1 | 8/2004 | Barkalow et al. | |
| 2006/0024248 A1 | 2/2006 | Spengler | |
| 2006/0177384 A1 | 8/2006 | Brown | |
| 2007/0048369 A1 | 3/2007 | Foreman | |
| 2007/0104783 A1* | 5/2007 | Domb et al. | 424/464 |
| 2007/0128284 A1 | 6/2007 | Troha et al. | |

FOREIGN PATENT DOCUMENTS

| | | |
|---|---|---|
| EP | 0 449 782 | 10/1991 |
| WO | WO 00/59423 | 10/2000 |
| WO | WO 01/05388 | 1/2001 |
| WO | WO 2006/013081 | 2/2006 |

* cited by examiner

*Primary Examiner* — Snigdha Maewall
(74) *Attorney, Agent, or Firm* — Pabst Patent Group LLP

(57) ABSTRACT

Compositions for the treatment of xerostomia, and methods of making and using thereof are disclosed herein. The compositions are typically in the form of a film or tablet, such as a double layer sticker tablet. The compositions adhere to a buccal surface or mucosal surface in the oral cavity for at least 15 minutes, preferably for at least 30 minutes. The compositions themselves are able to increase the levels of saliva in the mouth without the need for active agents, such sialogogic agents. The compositions optionally contain a non-lipid lubricant, a flavoring agent, and/or a buffering agent. The composition is generally effective at treating or ameliorating the effects of xerostomia for a time period ranging from at least 30 minutes up to eight hours following administration to the buccal or oral mucosa.

18 Claims, 1 Drawing Sheet

ADHESIVE COMPOSITIONS FOR THE TREATMENT OF XEROSTOMIA

CROSS-REFERENCE TO RELATED APPLICATIONS

This application is a continuation-in-part of U.S. Ser. No. 11/959,997 entitled "Adhesive Compositions for the Treatment of Xerostomia", filed on Dec. 19, 2007, which claims priority to U.S. Ser. No. 60/957,899, filed Aug. 24, 2007.

FIELD OF THE INVENTION

This invention relates to compositions and methods for the treatment or amelioration of the effects of xerostomia.

BACKGROUND OF THE INVENTION

Saliva lubricates the mouth and also contains bacteriostatic and digestive agents. Strong tasting and dry foods are typically the most effective in stimulating saliva production. Saliva stimulation can also follow the consumption of distasteful materials, as a defensive response of the oral mucosa.

Xerostomia (dry mouth) is suffered by an estimated 20% or more of adults, most of whom are women, as a consequence of the inability to secrete saliva. The condition itself is uncomfortable, but may also have serious consequences, resulting in severe dental decay and/or oral infections. Dry mouth can be caused by a number of maladies, such as an autoimmune disease like Sjögren's syndrome, diabetes, AIDS, bone marrow transplantation or dehydration. It may also occur as a response to radiation treatment or as an unwanted side effect of drug treatments. It is thought that over 1,800 drugs have the capacity to cause dry mouth, when taken over a period of time. Dry mouth may also occur as a physiologic response (e.g. stress, nervousness, or "stage fright").

Individuals suffering from Sjögren's syndrome or other pathologic causes of xerostomia chronically lack the ability to salivate and have difficulty tasting, chewing, swallowing, and speaking. Severe cases of xerostomia can bring about heightened tooth decay and infections of the mouth.

Xerostomic individuals may benefit from drug treatment with pilocarpine, for example, which stimulates salivation. However, other secretory functions are heightened as well, which can include profuse sweating. In these cases, the curative treatment may be as objectionable as xerostomia.

Palliative treatments are generally short acting and cosmetic in nature, and include constant ingestion of water, the use of non-cariogenic candies or demulcents, or other agents to directly hydrate the oral cavity or to provide a lubricious mouthfeel. Traditional lozenges, such as candy or cough drops, begin to dissolve immediately upon placement in the oral cavity, and rapidly dissolve within a few minutes. Although individuals' responses to such treatments can vary, these treatments do not provide relief for the long-term and chronic nature of xerostomia.

There is anecdotal evidence that some traditional herbal or natural products may stimulate salivation. For the most part, these reports concern the chewing of plant materials such as stems, bark, seeds, and leaves, etc. Some plant materials used have broadly stimulating properties, such as betel, khat, tobacco and cola nuts. Most plant materials have strong tastes, such as sour tasting lemon and citrus peel, and bitter tasting wormwood, golden seal and yarrow stems, or contain unpleasant-tasting irritants, such as the resins of gum myrrh and the pepper of kava and prickly ash bark.

Compositions for the treatment of plaque, which are also capable of stimulating the production of saliva, require abrasive materials. For example, U.S. Pat. No. 5,804,165 to Arnold discloses an anti-plaque oral composition containing a source of carbon dioxide, silica, and xylitol where the carbon dioxide comes from a bicarbonate. The tablet converts to a solid silica-containing suspension in the saliva of an oral cavity (see also U.S. Pat. Nos. 5,817,294; 5,965,110; and 6,086,854, all to Arnold). The presence of abrasive materials, such as silica, however, may harm the dry mucosal tissue, if administered to a patient suffering from xerostomia. Additionally, these compositions only provide a short-term effect.

Bioadhesive sticker tablets for the treatment of oral disorders, such as ulcers or legions are disclosed in U.S. Publication No. 2007/0104783 to Domb, et al. However, the tablets are not indicated for the treatment of xerostomia.

Treatments of xerostomia have been directed toward the control of dental decay, relief of symptoms, and increased salivary flow. The currently available treatments range from over the counter (OTC) medications to prescription drugs. Effective drugs appear to be few; and a large number of prescription drugs cause or exacerbate xerostomia.

Artificial saliva and saliva substitutes are available in the form of solutions, sprays and lozenges to replace moisture and lubricate the mouth; however, they must be used frequently and consistently as they do not stimulate salivary function.

U.S. Pat. No. 5,580,880 to Handa, et al., U.S. Pat. No. 5,686,094 to Acharya, U.S. Pat. No. 5,962,503 to Ekstrom, et al., and U.S. Pat. No. 7,198,779 to Rifa Pinol, et al., disclose compositions containing spirooxathiolane-quinone, polycarbophil, cholinesterase inhibitors, and a combination of saline saliva stimulating substitute agents, saliva production stimulating agent, oral antiseptic and oral mucosal protective agents respectively, for the treatment of xersotomia. However, these compositions do not remain long in the mouth and do not produce a long-lasting effect.

There has been some success clinical reported in treating xerostomia. However, given the large number of patients suffering from xerostomia each year, in addition to the larger number of patients undergoing cancer therapy, who often receive multiple cycles of radiation therapy and/or chemotherapy, there is a need for improved treatments for xerostomia. Further, many current treatments provide unpleasant side effects, such as profuse sweating, or require multiple administrations throughout the day to be effective.

It is therefore an object of the invention to provide improved compositions for the treatment of xerostomia and methods of use thereof.

SUMMARY OF THE INVENTION

Compositions for the treatment of xerostomia, and methods of making and using thereof are disclosed herein. The compositions can be administered to individuals having the physiologic ability to salivate but who do not salivate in sufficient quantity to satisfy their personal comfort level of oral hydration. The compositions are typically in the form of a tablet. In one embodiment, the composition is in the form of a sticker tablet, such as a double layer sticker tablet. The compositions adhere to a buccal surface or mucosal surface in the oral cavity with full dissolution after at least about 15 minutes, preferably thirty minutes, most preferably at least about four hours. The dissolution of the composition results in increased salivation without the need for sialogogic agents or lubricants, although these may be included. The compositions optionally contain a non-lipid lubricant, a flavoring agent, and/or a buffering agent. In a preferred embodiment, the composition contains one or more bioadhesive materials, one or more buffering agents, one or more flavoring and/or coloring agents, and one non-lipid lubricant. In one embodiment, the composition does not contain a sialogogic agent or a lipid.

The methods for treatment of xerostomia require placing the composition on the oral mucosa of a patient's mouth, preferably on the palate or the cheek. The composition will adhere to the mucosal surface, and dissolve, for at least about 15-30 minutes, preferably about two to four hours. The composition is generally effective for treating or ameliorating the effects of xerostomia for a time period ranging from at least about 30 minutes up to about eight hours following administration to the buccal or oral mucosa.

DETAILED DESCRIPTION OF THE INVENTION

I. Definitions

Figure 1:
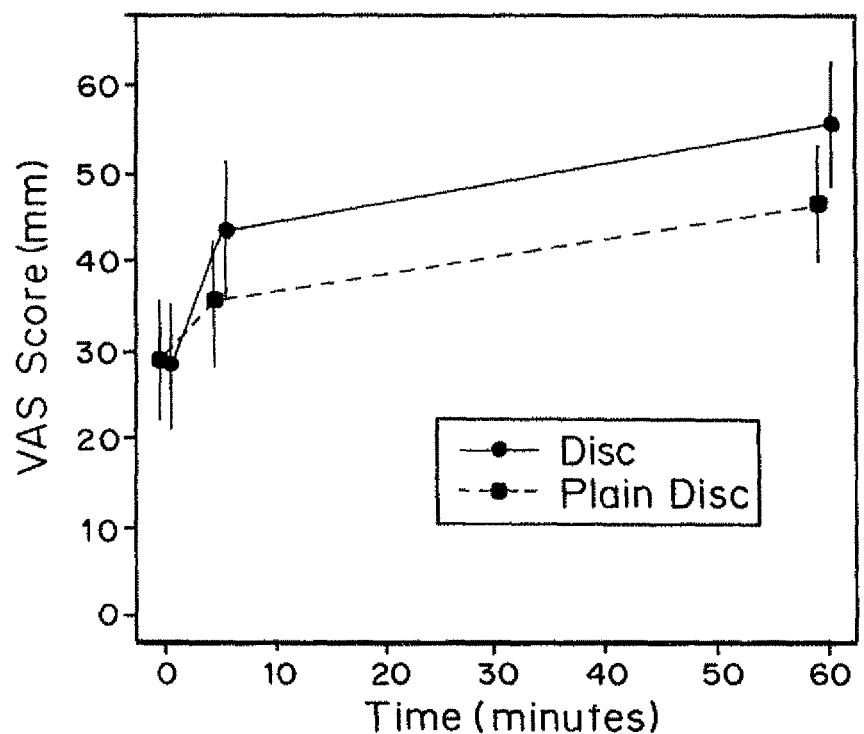
FIG. 1 is a graph of the VAS score (mm) over time in minutes for a disk as described herein (circle) as compared to a plain disk (square).

"Biocompatible", as generally used herein, means not having toxic or injurious effects on biological function in humans.

"Bioadhesive" and "mucoadhesive" are used interchangeably, and, as generally used herein, refers to a material which attaches, and preferably strongly attaches, to mucosal tissue upon hydration. The material must be capable of remaining adhered to the tissue in moist or wet in vivo environments. The compositions described herein are "self-bioadhesive" in that they attach to the site of interest without the need to reinforce attachment by way of another adhesive material. The strength of adherence can be measured by standard tests for measuring the force, e.g. in dynes per square centimeter, as disclosed in U.S. Pat. No. 4,615,697 to Robinson.

"Dissolution," as generally used herein, refers to the reduction of a solid dosage form of the present composition to a liquid form. More particularly, a complete dissolution of a solid dosage form refers to less than about 25% by weight of the solid dosage form remaining in the mouth following an appropriate time period, e.g., 15 minutes to four hours, after administration. Suitable methods are known in the art for determining the dissolution profile of a solid dosage form, e.g., the United States Pharmacopeia (USP) disintegration test. In embodiments wherein the tablet has multiple layers, the time required for "dissolution" can differ between the tablet layers, but complete dissolution refers to reduction of the solid dosage to form a liquid form for the entire tablet. In embodiments wherein the tablet contains non-dissolvable bioadhesive components, such as trays for whitening teeth kit, nicotine chewing gum etc., "dissolution" refers to the reduction of the solid dosage form of the present composition to a liquid form for the portions of the tablet which are formed of dissolvable components.

"Lipid", as generally used herein, refers to any fat-soluble (lipophilic) naturally-occurring or synthetic molecule.

"Lubricant," as generally used herein, refers to a substance which reduces friction. Lubricants can be synthetic or natural substances.

"Residence time," as generally used herein, refers to the duration of time the tablet adheres to a muscosal surface without complete dissolution. In embodiments wherein the composition is made of non-dissolvable bioadhesive materials such as those in nicotine chewing gum, "residence time" refers to the time until the non-dissolvable bioadhesive materials are removed from the oral cavity.

"Sialogogic agent", as generally used herein, refers to any material that induces and/or stimulates the flow of saliva in a patient's mouth.

"Xerostomia therapeutic agent", as generally used herein, refers to any agent that reduces the symptoms of xerostomia, including by providing comfort to the patient, such as by lubricating the mouth and/or by inducing saliva production. Xerostomia therapeutic agent is a general category that includes sialogogic agents and agents that do not induce saliva production, but improve the patient's comfort. For example, lipids that lubricate the mouth provide comfort to the patient without inducing saliva production.

II. Compositions

Compositions for increasing the saliva levels in the mouth are described herein. The compositions contain one or more bioadhesive materials. The compositions themselves are able to increase the levels of saliva in the mouth without the need for sialogogic agents. In some embodiments, the compositions may further contain a buffering compound and/or a xerostomia therapeutic agent, which is neither a sialogogic agent nor a lipid, such as, for example, oral cavity enzymes, buffering salts to prevent the pH from dropping too low, glycerin, artificial saliva, antibacterial, odor, flavors etc. Alternatively, the compositions may also contain one or more lubricants.

The compositions stimulate the production of saliva in the patient for a prolonged period. The compositions further ameliorate dry mouth by delivering a long lasting demulcent property after the initial stimulation of salivation. Typically, the compositions soothe the patient's mouth and maintain a moist oral cavity for at least 30 minutes following administration, preferably for at least 60 minutes following administration, more preferably for at least three hours following administration, still more preferably for at least four hours following administration, up to eight hours following administration

A. Bioadhesive Materials

The compositions described herein contain one or more bioadhesive materials, and require sufficient retention times in the oral or mucosal cavity to provide extended relief for xerostomia before complete dissolution. To meet this requirement, the bioadhesive compositions preferably include an anionic polymer. The anionic polymer should have a large number of hydrophilic, polar groups, such as the carboxylic acids pendant on carboxyvinyl polymers. In preferred embodiments, carboxylic acid content should be between about 50% to about 80%, more preferably between about 56% and about 68%, when assayed by standard techniques.

Suitable bioadhesive materials include, but are not limited to, carboxylic acid-containing polymers such as copolymers of acrylic or methacrylic acid; esterified polyacrylic acid polymers, such as polyacrylic acid polymers lightly crosslinked with a polyalkenyl polyethers (commercially available from B.F. Goodrich, Cincinnati, Ohio, under the trademarks CARBOPOL® 934, 934P, 974, 940 and 941); maleic acid copolymers; polysaccharides such as karaya gum, tragacanth gum, xanthan gum, jaraya gum, pectin, guar gum, locust bean gum, psyllium seed gum, alginates, hydrocolloid gels prepared from polysaccharides extracted from Fronia elephantum, Sapindus trifoliatus, Kunjac, and the cashew tree; cellulose and cellulose derivatives such as carboxymethyl cellulose, hydroxypropyl cellulose (HPC, Klucel®), mixtures thereof, and mixtures of sulfated sucrose and aluminum hydroxide, along with other substances known for use in transdermal preparations capable of forming a solid colloid that can adhere to tissue, used alone or in combination with other suitable carriers.

A preferred bioadhesive is CARBOPOL® 934 or an equivalent, and is a water-soluble polymer of acrylic acid crosslinked with about 1% of a polyallyl ether of sucrose having an average of about 5.8 allyl groups for each sucrose molecule.

In preferred embodiments, the bioadhesive material is also a non-lipid, non-sialogogic xerostomia therapeutic agent. Examples of bioadhesive materials which are also non-lipid, non-sialogogic xerostomia therapeutic agents include, but are not limited to, esterified polyacrylic acid polymers (CARBOPOL® 934, 934P, 974, 940 and 941), cellulose and cellulose derivatives (carboxymethyl cellulose, hydroxypropyl cellulose), and combinations thereof.

In some embodiments, the bioadhesive materials contain at least one crosslinked polyacrylic acid, such as CARBOPOL® 934 or 971. In a preferred embodiment, the bioadhesive material is a mixture of crosslinked polyacrylic acid, i.e. CARBOPOL® 934, and hydroxypropyl cellulose (HPC).

The concentration of the bioadhesive materials in the composition ranges from 5% to 50% by weight of the tablet, preferably from about 10-20% by weight of the of the tablet. The concentration of the tablet is typically from about 40% to about 100% by weight of a single layer tablet.

In some embodiments, the composition is a double layer tablet containing a bioadhesive layer. The bioadhesive materials in the bioadhesive layer are present in 10% to 100% by weight of the bioadhesive layer, preferably from about 10% to 50% by weight of the bioadhesive layer, most preferably about 45% by weight of the bioadhesive layer.

B. Buffering Compounds

The composition typically includes one or more buffering compounds in an effective amount to maintain a neutral pH in the oral cavity for at least 30 minutes following administration. As the composition dissolves in the oral cavity, it generates a buffered solution in the oral cavity which, by maintaining a relatively neutral pH, can help to diminish the formation of caries and renders the oral cavity less prone to infection.

Preferred buffering compounds include disodium hydrogen phosphate, calcium chloride, citric acid, sodium citrate or potassium citrate, sodium acetate, ethanolamine, or a combination thereof. Other suitable buffering compounds include acids, such as fumaric acid, tartaric acid, malic acid, adipic acid, and other edible acids or their pharmaceutically acceptable salts can be used. Sodium carbonate and sodium bicarbonate are the preferred carbonate salts. However carbonates and bicarbonates of potassium, sodium, ammonium, magnesium, and calcium can also be used. The composition may contain from about 1% to about 10% by weight of the buffering compound.

The composition optionally includes one or more excipients which increase the time period during which the buffered solution remains in the oral cavity, as compared to the same composition in the absence of such excipients. Exemplary excipients include, but are not limited to, glycerin, polymers including, but not limited to, natural gums including Xanthan (e.g., 0.5 to 15% by weight), cellulose based materials such as methylcellulose, carboxymethylcellulose, hydroxypropylmethyl cellulose, hydroxyethyl cellulose (e.g., 0.2% to 40% by weight), acrylic acids including crosslinked and non-cross linked acrylic polymers, (e.g., 0.2% to 50% by weight), polyethylene glycols (e.g., 0.2% to 2% by weight), dextran (e.g., 0.05% to 0.5% by weight), gelatin (e.g., 0.2% to 5% by weight), polyvinyl alcohol (e.g., 0.1% to 5% by weight), polysorbate 80 (e.g., 0.2% to 2% by weight), and povidone (e.g., 0.1% to 4% by weight).

C. Lubricants i. Non-Lipid Lubricants

In some embodiments, the compositions include non-lipid lubricants. Non-lipid lubricants should be food-grade materials. Suitable non-lipid lubricants include, but are not limited to, hydrogels, such as CARBOPOL® (Lubrizol Advanced Materials, Inc.) which are polymers of acrylic acid crosslinked with allyl sucrose or allyl pentaerythritol, and copolymers of acrylic acid and $C_{10}$-$C_{30}$ alkyl acrylate crosslinked with allyl, water soluble polymers such as polyethylene glycol (molecular weight from 400-1,000,000), glycerol, polypropylene glycol, polyvinyl alcohol, polyvinyl pyrrolidone ("PVP") (e.g. PVP K-30 and/or PVP K-90), sodium benzoate, leucine, magnesium stearate, sodium lauryl sulfate, and sodium lauryl sulfoacetate. The concentration of the non-lipid lubricant is from about 3% (wt/wt) to about 80% (wt/wt). In a preferred embodiment, the non-lipid lubricant is present from about 40% (wt/wt) to about 70% (wt/wt). In a more preferred embodiment, the non-lipid lubricant is present in about 66% (wt/wt). In embodiments wherein the composition is in the form of a double layer tablet, the non-lipid lubricant is present in the bioadhesive layer from about 10% (wt/wt) to about 50% (wt/wt), more preferably from about 20% (wt/wt) to about 40% (wt/wt), and most preferably in about 37% (wt/wt).

ii. Lipid Lubricants

In some embodiments, the compositions contain one or more lipids. Lipids include fatty-acids and their derivatives (including tri-, di-, and monoglycerides and phospholipids), fatty alcohols and their derivatives, as well as other fat-soluble sterol-containing metabolites such as cholesterol. In other embodiments, the lipid lubricant is a triglyceride, including, but not limited to, tricaprin, trilaurin, triacetin, trimpistin, and triolein. In other embodiments, the lipid lubricant is a phospholipid, including, but are not limited to, phosphoglycerides (e.g. phosphatidyl serine, phosphatidyl inositol, phosphatidyl ethanolamine, and phosphatidyl choline) and sphingomyelin.

Preferred lipids are generally those that melt at or around body temperature so that they are solid at room temperature, but semiliquid or liquid at body temperature. Examples of preferred lipids include, but are not limited to, tricaprin, ethyl stearate, short chain waxes, and partially hydrogenated plant oils, such as corn oil. Additional preferred lipids include mixtures or pure mono-, di-, and triglycerides, semisolid phospholipids and hydrophobic short chain polymers, such as polycaprolactone.

The compositions contain an effective amount of the lipid to reduce friction and lubricate the mouth following administration of the composition to a patient suffering from xerostomia. The concentration of the lipid in the composition is at least about 5% by weight of the composition, and is no greater than about 50% by weight. Preferably the composition contains at least about 10% by weight of lipid, and more preferably the concentration of lipid in the composition ranges from about 10% to about 30% (wt/wt).

D. Active Agents i. Non-Sialogogic Xerostomia Therapeutic Agents

In preferred embodiments, the compositions themselves are made of xerostomia therapeutic agents, i.e. CARBOPOL® 934 or equivalents. In other embodiments, the compositions further include one or more non-sialogogic, xerostomia therapeutic agents for the treatment of xerostomia. Examples of suitable non-sialogogic xerostomic therapeutic agents include, but are not limited to, hyaluronic acid, chondroitin sulfate, coenzyme Q, spirooxathiolane-quinone, polycarbophil, oral antiseptics and oral mucosal protective agents. Additional agents include natural oil, essential oils, herbal medicaments, Mucopolysaccharide Solutions, Sodium fluoride, Lubricants such as Orajel® or Vaseline®, Carboxymethyl, or hydroxyethylcellulose solutions.

ii. Sialogogic Agents

The compositions may contain one or more sialogogic agents. Sialogogic agents that are useful in the composition include plant- or herb-based products. The agent may be flavored or flavorless, such as flavorless chemical agents. Sialogogic agents may be flavored, but the physiologic response to a sialogogic agent does not depend upon the presence of a flavor per se. Some flavored sialogogic agents are also spices. Additionally, chemicals with no characteristic or distinctive taste may be effective in stimulating salivation. This is the case with chemical agents such as the OPTAMINT®, a food additive based on peppermint extract, or OPTAFLOW®, a food additive containing several flavoring agents and food components.

Flavoring agents can also be used in conjunction with compounds having conventional sialogogic properties. Flavorless chemical sialogogic agents include, but are not limited to, citric acid, citrus oils, and ascorbic acid. Suitable plant- or herb-based sialogogic agents include, but are not limited to cardamom, ginger, licorice, mint extract, and anise.

Sialogogic agents also include pharmaceuticals, such as pilocarpine, cevimeline, anethole trithione, yohimbine, human interferon alpha and amifostine. Pilocarpine is a cholinergic parasympathomimetic agent, which may stimulate salivary flow and produce clinical benefits in some patients as well as cause adverse effects with other drugs. Cevimeline, a cholinergic agonist, is another systemic agent that appears to alleviate xerostomia in certain patient populations. Anethole trithione is a cholagogue that stimulates salivary flow in drug-induced xerostomia. Yolimbine is an alpha-2 adrenergic antagonist that can increase saliva flow. Additional suitable sialogogic agents include sulfur-containing antioxidants, as described in U.S. Publication No. 2007/0128284 to Troha, et al.

Sialogogic agents also include biological agents, such as probiotic bacteria, including but not limited to strains of various species of the genera *Bifidobacterium* and *Lactobacillus*.

The sialogogic agent is included in an amount to deliver safe (i.e. non-toxic) amounts of the agent as established in the pharmaceutical literature, such as *Martindale: The Complete Drug Reference* (Pharmaceutical Press). The sialogogic agent should be released from the tablet following administration to the mouth cavity, particularly to the sites where salivary glands are located. The tablet contains a sufficient dose of the sialogogic agent such that the agent is released for the desired time period at an effective amount to treat or alleviate symptoms of xerostomia. The effective amount is typical for each sialogogic agent. The desired release profile is also related to the sialogogic agent, and can be determined through standard means by one of ordinary skill in the art. The tablet should not contain a dose of the sialogogic agent that is greater than the necessary dose for administration since over-dosing may cause patient discomfort or undesirable side effects, such as burning of the mucosal tissue by for example a local overdose of menthol.

Typical doses for biological agents, such as probiotic bacteria, range from about 0.1 microgram to a few milligrams in the tablet or film, depending on the activity of the dry substance and the desired effect.

E. Carriers, Additives and Other Excipients i. Carriers

Compositions are prepared using a pharmaceutically acceptable carrier composed of materials that are considered safe and effective and may be administered to an individual without causing undesirable biological side effects or unwanted interactions. The term "carrier" includes, but is not limited, to diluents, binders, stabilizers, flavoring agents, pigments, humectants, disintegrators, and fillers.

ii. Humectants

Suitable humectants include, but are not limited to, edible polyhydric alcohols, such as glycerin, sorbitol, xylitol, butylene glycol, polyethylene glycol, and propylene glycol. In one embodiment, the humectant is sorbitol and/or glycerin. The humectant may also act as a plasticizer to provide a flexible sticker, which is comfortable to the user when placed in his/her mouth. The concentration of the humectant is from about 1% to about 20% by weight of the composition, preferably from about 1% to about % by weight of the composition.

iii. Flavoring Agents

Preferably the composition contains one or more flavoring agents, such as natural or artificial sweeteners. This is particularly preferred if the xerostomia therapeutic agent is flavorless or has an unpleasant taste.

Suitable flavoring agents include, but are limited to, oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and combinations thereof. The concentration of the flavoring agent is from about 0.001% to about 1% by weight of the composition. Some of the compounds listed as excipients and carriers can also be sialogogic agents depending on the concentration of the compound in the composition. For example, menthol at a concentration of 0.01% by weight is typically a flavoring agent but at a concentration of 2.0% by weight can be a sialogogic active agent.

Natural or artificial sweeteners include, but are not limited to, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and combinations thereof. Preferably the sweetener is a non-cariogenic sugar alcohol. The concentration of the sweetener is from about 0.1% to about 5% by weight of the composition, preferably about 4% by weight of the composition, although concentrations as great as 40% may be used.

Flavoring agents (including sweeteners) are present in the tablet at 0.1% to 5% by weight, depending on the specific flavor and desired attributes. If plant-based or herb-based sialogogic agents are incorporated into the compositions, these may be included at 0.25% to 20% of the composition by weight. Artificial sweeteners are used according to taste, and generally the composition contains at least 0.1% (wt/wt) of an artificial sweetener.

iv. Binders

Tabletting materials such as binders, fillers, and flow aids typically accounts for about 90% of the mass, and comprises mostly sugar alcohols, but includes flow aids, lubricants, flavors and excipients. Suitable binders include sorbitol, lactose, urea, sucrose stearate, starch, maltodextrin, corn syrup solids, sodium citrate, sodium sulfate, sodium chloride, sucrose, and dextrates. The composition contains at least 0.1% (wt/wt) of a binder.

v. Additional Additives

Desensitizing agents may also be added, such as strontium nitrate and potassium nitrate, to reduce heat or cold sensitivity.

Antimicrobial agents such as cetylpyridinium chloride and domiphen bromide may be added to reduce bacterial levels in the oral cavity.

Breath freshening ingredients such as chlorophyll may be added and pharmaceutical agents such as antibiotics may also be included in the compositions.

Non-limiting examples of some other components that may be included in a delivery composition include one or more of the following: penetration enhancers, stabilizers for the xerostomia therapeutic, preservatives such as antioxidants, butylated hydroxytoluene, antifungals, and antibacterials.

F. Forms of the Composition

The compositions can be in form of a single layer, double layer, or multilayer tablet, which can be prepared using conventional methods known in the art, such as by compression tabletting. In one embodiment, the tablet is a single layer table. In another embodiment, the tablet is a double layer tablet. In a preferred embodiment, the composition is a double layer bioadhesive tablet. The tablet may contain an acceptable plasticizer for the bioadhesive material, and a cohesive or binding agent.

The total mass of the sticker tablet generally ranges from 50 mg to 1000 mg, depending on particular consumer preferences and desired performance attributes such as composition residence time in the mouth. The preferred mass ranges from 200 mg to 400 mg.

The tablets can be of any suitable size for placement in a patient's mouth. In one embodiment, the surface area of the tablet is from about 0.4 cm$^2$ to about 3 cm$^2$, preferably from about 0.5 cm$^2$ to 1.8 cm$^2$, more preferably from 0.5 cm$^2$ to 1.2 cm$^2$. For example, a tablet having a diameter of 15 mm, will have a surface area of approximately 1.8 cm$^2$. In the most preferred embodiment, the tablet has a suitable geometry for placement on the desired surface in the mouth. For example, for placement on the palate, the table preferably contains a convex surface designed to be placed adjacent to and adhere to the palate. In a double layer tablet, this side corresponds with the outer surface of the bioadhesive layer of the tablet. Tablets are typically round or oval, with a diameter up to 3 cm.

In a preferred embodiment, the bioadhesive sticker tablet or film contains 10-20 wt. % CARBOPOL® 934 or CARBOPOL® 971 (as a non-lipid, non-sialogogic xerostomia therapeutic agent), 1-4 wt. % calcium chloride, 10-40 wt. % non-cariogenic sugar alcohol (as a flavoring agent), 1-3 wt. % sodium bicarbonate, 5-40 wt. % binder, and 1-15 wt. % polymer or gum (as a lubricant).

III. Methods of Administering the Compositions

The sticker tablet is applied to the oral mucosa to treat xerostomia. Preferably the tablet is placed on the palate of the mouth cavity; however it may be placed in any suitable mucosal tissue inside the mouth, such as on the cheek The sticker tablet is preferably administered from about once a day to four times per day, more preferably from about once per day to about twice per day. In some treatments, the patient will rest for a suitable period of time between applications of the tablet or film to allow natural activity of the mouth organs. Additionally or alternatively, in the preferred embodiment, the tablet should be attached in different locations in the patient's mouth for consecutive treatments to minimize local mucosal irritation and provide relief to the immediately prior adhesion site. For example, one tablet may be placed at a first location, such as the palate; for the second treatment, the tablet may be placed in a different location, such as on the buccal mucosa, and for a subsequent treatment, the tablet may be placed at the first location (e.g. the palate) or a location different from both the first and second placement locations.

Tablets of different compositions may be placed in the mouth to allow different stimulations of the salivary glands or effects on mucosal tissues.

In severe cases of xerostomia, or when small tablets are used, two or more tablets can be places in different locations simultaneously. However, typically treatment will require placement of one tablet at a time in the mouth.

A. Composition Residence

In some embodiments, the bioadhesive tablet adheres to the buccal or mucosal surface, such as on the palate or cheek, with a residence time of at least 15 minutes following administration. In other embodiments, the residence time of the bioadhesive tablet is from about 15 minutes to about 12 hours, more preferably from about 15 minutes to eight hours. Typically the individual determines the length of time of residence by feeling the presence of the tablet.

In one embodiment, residence time is determined by complete dissolution of the tablet. In these cases, residence time is at least equal to dissolution time. In another embodiment, non-dissolvable portions of the tablet are physically removed by a medical professional or the individual user. In these embodiments, residence time can be greater than dissolution time.

B. Composition Dissolution

In preferred embodiments, the composition does not fully dissolve for at least 15 minutes following administration to the buccal or oral mucosa, more preferably for at least 30 minutes following administration following administration, and most preferably for up to eight hours following administration.

In some embodiments, the layers of a multi-layer tablet will dissolve concurrently following administration to a buccal or mucosal cavity. In other embodiments, layers of a multi-layer tablet dissolve with different dissolution times following administration. In yet other embodiments, one or more layers of the tablet dissolve after administration, but other layers, the mucoadhesive layer for example, does not dissolve.

C. Therapeutic Effectiveness

The compositions described herein offer both immediate and extended relief to an individual suffering from xerostomia. Upon placement of the composition in the buccal or mucosal cavity, the composition begins to dissolve, providing the individual with relief for at least about 15 minutes following administration. More preferably, xerostomia relief is provided for from about 30 minutes to eight hours following adherence of the tablet or film.

It is believed that the tablets are effective at treating or ameliorating the severity of symptoms associated with xerostomia by protecting superficial salivary function, stimulating salivary flow and/or decreasing the viscosity of saliva. Relief from xerostomia can be measured by increasing objective salivary flow rate, subjective salivary flow rate, and/or mouth dryness at various time points following administration, 30 minutes or one hour, for example.

Maintenance of a moist oral cavity is important for the preservation of good oral hygiene. A dry mouth is susceptible to infection and other conditions, such as gingivitis, yeast, caries, mucositis, halitosis, and related conditions such as sore throat, and itchy/scratchy throat as in allergic responses, which inadequate mouth pH control and moisture content can exacerbate. Thus, in addition to the direct treatment of xerostomia, these compositions can complement therapeutic approaches to maintaining good oral health.

IV. Method of Making the Compositions

A. Compression Molding

Compression molding can be used to prepare single layer, dual layer, or multilayer sticker tablets. The simplest method for preparing the sticker tablets is by compression molding using a single or multi-punch press machine. The powder is loaded in the punch having a diameter ranging from about 4 to about 15 mm and a thickness of about 0.5 mm to about 2.5 mm. The thickness is defined by the amount of powder added, usually between about 50 mg and 250 mg. The powder is compressed to form a single layer sticker tablet.

Double layer sticker tablets are prepared using the double compression technique. The inert powder is first added to the punch to cover the surface. The formulation powder is added on top and compression is applied to produce a sticker tablet where one side is bioadhesive and the other is not. The non-bioadhesive side also tends to be less water-permeable than the bioadhesive side. Alternatively, one powder is added to the punch and compressed to form a thin tablet. The second powder is then added and compressed to form a uniform bilayer tablet.

B. Spray Coating

Double layer sticker tablets can also be prepared by spray coating. In the spray coating method, the coating is applied by spraying an alcoholic solution or fine dispersion of a hydrophobic coating material onto one side of the sticker tablet. The spray coating can be applied using an automated machine where the tablets are placed onto a running sheet which is exposed to spray nozzles to spray coat the tablets. Typical hydrophobic powders suitable for this coating include: fatty acids and salts such as Mg- or Ca-stearate, triglycerides and fatty acid esters, ethyl cellulose, methyl methacrylate-methacrylic acid copolymers (EUDRAGIT®), and other pharmaceutically acceptable hydrophobic components.

C. Solvent Casting

Another way of preparing thin single layer sticker tablets is by casting a concentrated suspension in ethanol of all tablet ingredients onto a flat surface where, after solvent evaporation, a thin sheet is obtained. The sheet is then cut into films of the desired size and shape using a cutting mold.

Double layer films can be prepared by applying the coating as a spray on top of the sheet loaded with the active agents. Other industrial methods can be used, such as forming the sheet on an edible hydrophobic sheet such as rice paper and cutting the sheets into the desired size.

D. Controlled Release Compositions

In some embodiments, the tablet or film is designed for controlled release of the sialogogic agent.

In one embodiment, a sialogogic agent is absorbed in or onto a polymeric component or is encapsulated into microcapsules that control the release of the agent when embedded in the tablet. For example, a solution (e.g. ethanolic solution) of a sialogogic herbal extract may be absorbed in a polymer matrix, such as crosslinked polyacrylic acid (e.g. CARBOPOLS), hydroxyl propyl cellulose (HPC), ethyl cellulose or EUDRAGIT® powders, and added to the tablet mixture, preferably on the outer layer.

Encapsulation of sialogogic agents in matrix type or capsule type particles can be done via standard methods used in the pharmaceutical industry. Encapsulating materials include, but are not limited to, ethyl cellulose, copolymers of methacrylic acid and methyl methacrylate, gelatin, alginates, gum polysaccharides, polycyanoacrylate, etc.

Encapsulation processes are selected or designed taking into consideration the heat sensitivity and the low melting or boiling point and/or the sublimation temperature of the sialogogic agents of interest.

E. Inclusion of Biological Agents in Tablet or Film

When biological agents, such as probiotic agents and enzymes, are included in the tablet or film, they are typically incorporated as a dry powder. Prior to the addition of the biological agents to the other materials for the formation of the tablet or film, the biological agents may be stabilized with a mixture of amino acids, salts, and acidic and basic small molecules, may be encapsulated in a polymeric carrier or may be absorbed in a pharmaceutically acceptable excipient or additive, such as polysaccharides or acrylate-based polymers.

EXAMPLES

Example 1

Research and Clinical Trials Testing Friability, Dissolution Time and Efficacy for Bioadhesive Tablets for Treatment of Xerostomia Compositions and Methods of Manufacture Eight (8) bioadhesive double-layer sticker tablets containing different amounts of lipid (i.e. Tricaprin), sialogogic agent, etc., as described in Table 1, were prepared.

The first layer in the tablet was an adhesive layer that contained 30 mg of Carbopol 940 and 10 mg of hydroxy propyl cellulose (HPC). The second layer was formed from a mixture of polyvinylpyrrolidone (PVP), xylitol, tricaprin, lemon flavor and CARBOPOL® 940. The tablet was prepared in two steps, and the adhesive layer was placed on top of the second layer containing the sialogogic agent. The total weight for each tablet was about 240 mg.

The second layer also contained a pink dye commonly used in food to distinguish this layer from the first, bioadhesive layer. Also, the tablet was convex on the side containing the adhesive layer and flat on the side containing the layer containing the sialogogic agent. This design enabled the table to fit snugly on the palate in the mouth.

TABLE 1

Composition of Layer containing the Sialogogic Agent in Bioadhesive Double-layer Sticker Tablets

| Composition | Tablet Number | | | | | | | |
|---|---|---|---|---|---|---|---|---|
| | 1 | 2 | 3 | 4 | 5 | 6 | 7 | 8 |
| Calcium chloride (% w/w) | 5 | 5 | 5 | 5 | 5 | 5 | 5 | 5 |
| Xylitol (% w/w) | 44.5 | 44.5 | 44.5 | 33.5 | 44.5 | 38.5 | 32.5 | 26.5 |
| PVP K-90 (% w/w) | — | 30 | 15 | 51 | 30 | 26 | 22 | 18 |

TABLE 1-continued

Composition of Layer containing the Sialogogic Agent in Bioadhesive Double-layer Sticker Tablets

| Composition | Tablet Number | | | | | | | |
|---|---|---|---|---|---|---|---|---|
| | 1 | 2 | 3 | 4 | 5 | 6 | 7 | 8 |
| PVP K-30 (% w/w) | 30 | — | 15 | — | — | — | — | — |
| Tricaprin (% w/w) | 20 | 20 | 20 | 10 | 20 | 30 | 40 | 50 |
| Trilaurin (% w/w) | — | — | — | — | — | — | — | — |
| Lemon flavor (% w/w) | 0.5 | 0.5 | 0.5 | 0.5 | 0.5 | 0.5 | 0.5 | 0.5 |
| Total (% w/w) | 100 | 100 | 100 | 100 | 100 | 100 | 100 | 100 |

The components in the non-adhesive layer included:

polyvinylpyrrolidone (PVP) (K-value of 30 or 90)—a binding agent with hydrophilic lubricating affect (i.e. a non-lipid lubricating agent), xylitol—a sweetener and humectant, tricaprin—lipid that melts at body temperature, lemon flavor—a sialogogic agent, and calcium chloride—a buffering agent.

Friability and Dissolution Test

For the friability and dissolution tests, three (3) tablets were tested for each tablet number. Friability tests were performed by using a universal friability test and according to the USP. Time of dissolution was determined by placing one tablet in a vial followed by the addition of 15 mL phosphate buffer (pH 6.5) at 37° C. Buffer was replaced every 10 minutes with fresh buffer. Results for the friability and dissolution tests are provided in Table 2. Dissolution times ranged up to about four hours.

TABLE 2

Results of Friability and Dissolution Tests

| Tablet No. | Short Name for Tablet | Friability | Time of dissolution (min) |
|---|---|---|---|
| 1 | 30% PVP-K30 | 0.6 ± 0.1 | 10.5 ± 1 |
| 2 | 30% PVP-K90 | 0.26 ± 0.05 | 27.5 ± 2.5 |
| 3 | Mixture PVP K30:K90 (1:1) | 0.35 ± 0.04 | 52.5 ± 2.5 |
| 4 | 10% lipid | 0.26 ± 0.11 | 52.5 ± 2 |
| 5 | 20% lipid | 0.26 ± 0.05 | 49 ± 1 |
| 6 | 30% lipid | 0.16 ± 0.05 | 43 ± 1 |
| 7 | 40% lipid | 0.23 ± 0.03 | 24.5 ± 1 |
| 8 | 50% lipid | 0.62 ± 0.12 | 10.5 ± 1 |

As shown in Table 2, Tablet 1, which contained 30% (wt/wt) PVP K-30 as a non-lipid lubricating material, was more friable and dissolved much faster than Tablets 2 and 3, which contained 30% (wt/wt) PVP K-90 and 30% (wt/wt) of a 1:1 mixture of PVP K-30 and PVP K-90, respectively.

Further, Tablets 4-6, which contained 10%, 20% and 30% (wt/wt) lipid, respectively had approximately the same friability and similar dissolution times. Although Tablet 7, which contained 40% (wt/wt) lipid had a similar friability to Tablets 4-6, it dissolved much more quickly (within about 24.5 minutes). Finally, Tablet 8, which contained the highest amount of lipid was also the most friable and dissolved the fastest of Tablets 4-8 (within about 10.5 minutes). Tablets 5 and 6 were selected for further research and development.

Clinical Study

Patients

Double layer sticker tablet having the composition of Tablet 5 (see Table 1) were tested in the following clinical study. The clinical study was conducted in the School of Dentistry, at The Hebrew University, Jerusalem, Israel. The protocol was approved by the institutional review board of Hadassah Hospital. 22 patients were tested. All patients gave written informed consent before entry and before study-related procedures were performed.

Eligible xerostomic patients were at least 18 years of age, and suffered from dry mouth syndrome due to Sjogren's syndrome or due to previous treatment with head and neck radioiodine, or complained of dry mouth. Patients suffering from glaucoma, cardiac arrhythmias, pulmonary, bladder problems, or an autoimmune disease were excluded from the study. The mean age of the patients was 53 years and the age range was from 18 years to 72 years.

The study was conducted between 8:00 and 12:00 am, after 2 hours of free of food intake, mouthwash use or teeth brushing. Whole salivary flow was collected for 10 minutes before and at 1, 2, 3, and 6 hours after the application of one adhesive tablet. The adhesive tablet was placed by a dentist in the palate of the patient's mouth. Only one palate was placed in the mouth in this study. Systolic and diastolic blood pressure, heart rate, and body temperature were measured at each time point. The study was continued for 5 hours, during which time the patient's complaints and subjective feelings were recorded.

A control group of 10 patients was instructed to use a commercial spray (BIOTENE®, Laclede Professional Products, Inc. Rancho Dominguez, Calif. 90220 USA) about 3 to 5 times during the 5-hour long study. BIOTENE® mouthwash contains four antibacterial enzymes which boost the defense system normally found in the saliva.

Saliva sampling and pH measurement for various sites in the oral cavity were performed by one trained clinician, who was blinded to treatment sequence, before and after each treatment. On each occasion, sampling was performed in the morning to minimize bias due to diurnal variations in salivary flow. Unstimulated whole saliva (UWS) was collected by spitting any saliva into a sterile, pre-weighed container over a period of 5 minutes. Stimulated whole saliva (SWS) was collected by having the subject chew on a standard piece of sterilized silicone rubber tubing for 5 minutes and spitting all saliva into a sterile, pre-weighed container.

The weight of the UWS and SWS was recorded and the salivary flow rate determined and expressed as ml/min.

Patient satisfaction with aspects of oral comfort and function during the two treatments was explored by asking questions on mouth condition, speaking, chewing hard and soft foods, swallowing and comfort of the mouth. In addition, specific questions about ease of use of the Tablet treatment and the Control treatment were asked.

Responses were made using 100 mm Visual Analog Scale ("VAS") with anchor words: extremely difficult/no difficulty and totally unsatisfied/totally satisfied, as appropriate.

Statistical Analysis

Statistical comparisons of the findings were made by one-way analysis of variance. Comparison of means was performed by the least significant difference test. Data analysis was performed using a statistical software package (Instat; GraphPad Software, San Diego, Calif.). The significance level was set at $p<0.05$.

Results

The single-layer bioadhesive tablets improved objective and subjective scores compared to treatment with the control.

The administration of the single-layer bioadhesive tablets reduced the severity of xerostomia symptoms compared to the control and was the treatment of choice compared to the control.

A significant increase (p=0.03) in salivary flow rate was observed immediately (2-5 minutes) after adhering one tablet. Also after 1, 2, and 5 hours base line level of salivary flow was higher (p=0.03) following application of the tablet compared to following treatment with the control.

Control performance was 50% lower than results achieved following administration with the tablet in objective results, including saliva flow measurements. Whole saliva pH increased significantly among the patients given tablets (p=0.00) comparing to the control (p=0.04).

Patients' satisfactory and overall compliance was high for both treatments. However, the overall patient satisfaction score was higher for the tablet treatment compared to the control, and the majority of participants chose tablets as the preferred treatment.

Example 2

Comparative Testing of Two Bioadhesive Tablets

Two bilayer bioadhesive tablets, one containing a sialogogic agent and a lipid, and the other free of a sialogogic agent and a lipid were evaluated for efficacy in a clinical study.

Tablet Composition

The tablets had the following compositions:

| Tablet 1 (containing a sialogogic agent and a lipid) | |
| --- | --- |
| Layer A: | |
| Carbopol 934 or substitute, (Goodrich) | 30 mg |
| Klucel HF (HPC), (Hercules) | 15 mg |
| Polyvinylpyrrolidone K90, (FLUKA) | 37 mg |
| Xylitol/Carmine Pre mix* | 13 mg |
| Lemonade | 3 mg |
| Magnesium stearate | 2 mg |
| Total weight: | 100 mg |
| Layer B: | |
| Calcium carbonate | 15 mg |
| Sodium Chloride | 10 mg |
| Xylitol | 170 mg |
| Polyvinylpyrrolidone K-90 | 80 mg |
| MCT-70 | 30 mg |
| Citric acid | 20 mg |
| Silicone dioxide | 5 mg |
| Lemonade | 20 mg |
| Carbopol 934 or substitute, (Goodrich) | 38 mg |
| Enzymes: | |
| Lactoperoxidase | 750 Units |
| Glucose Oxidase | 500 Units |
| Lysozyme | 0.8 mg |
| Lactoferrin | 0.8 mg |
| Total weight: | 390 mg |

| Tablet 2 (free of a sialogogic agent and a lipid) | |
| --- | --- |
| Layer A: | |
| Carbopol 934 or substitute, (Goodrich) | 30 mg |
| Klucel HF (HPC), (Hercules) | 15 mg |
| Polyvinylpyrrolidone K90, (FLUKA) | 37 mg |
| Xylitol/Carmine Pre mix* | 13 mg |
| Magnesium stearate | 2 mg |
| Total weight: | 100 mg |
| Layer B: | |
| Calcium carbonate | 15 mg |
| Sodium Chloride | 10 mg |
| Polyvinylpyrrolidone K-90 | 180 mg |
| Silicone dioxide | 5 mg |
| Carbopol 934 or substitute, (Goodrich) | 25 mg |
| Total weight: | 235 mg |

The tablets were prepared in the following manner. The materials in Layer A, minus xylitol and carmine were mixed to form a homogeneous mixture. The mixture of xylitol and carmine was prepared separately Xylitol and carmine were dissolved in 10 mL distilled water to form an aqueous solution. The solution was placed in an oven and heated at about 100° C. until the water was removed to less than 0.1%. The resulting solid was pulverized to form a flowable red powder.

The ingredients in Layer B, minus Carbopol and the enzymes (in the case of Tablet 1), were mixed together. For the formation of Tablet 1, a sufficient amount of water was sprayed (about 5 mL to 100 g powder) over the mixture to form a paste. The paste was mixed to ensure homogeneity and dried under vacuum at room temperature over night. After drying, the resulting solid was milled (by a mill or by pestle and mortar), weighed, and the Carbopol (10 wt. %) and enzymes were added and the mixture was mixed well.

Tablet formation was performed using a double press machine. The Layer A mixture was added to the convex punch hole and press. The Layer B mixture was added on top of Layer A, and maximum pressure was applied. The tablets were placed in a well sealed container, purged with dry Nitrogen, and stored in a cold, dry location according to GMP requirements.

Clinical Study

A clinical study was performed to compare the efficacy of the two tablets. Twenty-five consenting eligible adults were enrolled in the study. A baseline cleaning was performed and standardized oral hygiene instruction was provided.

Methods

At Visit 2 (V2), objective measurements of whole salivary flow rates (mL/min) and halitosis, and subjective measurements of mouth dryness (VAS scores using Mouth Feel Questionnaire) were recorded at baseline and subjects began a one week "No Treatment-Wash-Out" period.

At Visit 3 (V3), subjects were randomized, into one of the two groups (Tablet 1, which contains a sialogogic agent and a lipid; and Tablet 2, which does not contain a sialogogic agent and a lipid). Objective measurements of whole salivary flow rates (mL/min) and halitosis, and subjective measurements of mouth dryness (VAS scores using Mouth Feel Questionnaire) were recorded at baseline, then 5 and 60 minutes after tablet application. Subjects were given a 1 week supply of tablets to use at home for 1 week.

At Visit 4 (V4), objective measurements of whole salivary flow rates (mL/min) and halitosis, and subjective measurements of mouth dryness (VAS scores using Mouth Feel Questionnaire) were recorded at baseline, then a cross-over occurred where subjects were given the other tablet, followed by measurements at 5 and 60 minutes after disc application.

At Visit 5 (V5), objective measurements of whole salivary flow rates (ml/min) and halitosis, and subjective measurements of mouth dryness (VAS scores using Mouth Feel Questionnaire) were recorded at baseline. Subjects took a short post-study questionnaire.

The primary endpoint of subjective complaints of a dry mouth (xerostomia) was assessed by comparing within subjects (a) baseline V2 to baseline V3, V4 & V5 and comparing (b) baseline V3 to 5 minutes and 60 minutes after application of tablet, and then baseline V4 to 5 minutes and 60 minutes after application of tablet. Particular emphasis was placed upon questions relating to oral dryness (Item #2 (moistness) & Item #4 (dryness)).

The secondary endpoints were assessed as follows:
1. The subjective experience of "fresh breath" by comparing (a) baseline V2 to baseline V3, V4 & V5 and comparing (b) baseline V3 to 5 minutes and 60 minutes after application of tablet, and then baseline V4 to 5 minutes and 60 minutes after application of tablet. Particular emphasis was placed upon questions relating to oral dryness (Q 1 (freshness) & Q5 (staleness)).
2. Objective assessment via measurement of modified unstimulated whole salivary flow rates and comparing (a) baseline V2 to baseline V3, V4 & V5, and comparing (b) baseline V3 to 5 minutes and 60 minutes after application of tablet, and then baseline V4 to 5 minutes and 60 minutes after application of tablet.
3. Objective assessment via measurement of halitosis comparing (a) baseline V2 to baseline V3, V4 & V5 VSC and (h) baseline V3 to >60 minutes after application of tablet and baseline V4 to >60 minutes after application of tablet.

Results 25 subjects completed the study. The demographic information is provided in Table 1.

TABLE 1

| Demographics | | |
|---|---|---|
| | (N = 25) | |
| | Male | Female |
| Gender Number | 8 | 17 |
| Mean age years (SD) | | 61 |

V2 vs V3 Baseline: "No-Treatment-Wash-Out" Week

Compared to baseline at V2, there were no significant within-subjects effects over the "No Treatment-Wash-Out" week (i.e., V3 for any of the primary or secondary baseline measures (analysis not shown).

V3 Baseline Vs Measures Over Time

This procedure examined the effects of the Intervention [Tablet 1 or 2] during V3 over Time [1=Baseline, 2=5 min, 3=60 min] for 2 primary output measures from the BMQ [Dryness=Vdry; Moistness=Vmoist] and a secondary objective measure, Salivary Flow rate [Vflow]. Results show a marginal (p=0.1016) difference on the Dryness measure for the two tablets. Results also show a statistically significant increase (p=0.0049) in perceived Moistness over Time for both tablets. However, there was no statistically significant difference in perceived moistness between the 2 groups.

As for the secondary measure, salivary flow rate, results show a statistically significant increase (p=0.0162) in salivary flow rate from baseline to 60 minutes after baseline for both tablets; but, there were no statistically significant differences between the two tablets.

V4 Baseline Vs Measures Over Time

This procedure examined the effects of the Intervention [Tablet 1 and Tablet 2] during V4 over Time [1=Baseline, 2=5 min, 3=60 min] for 2 primary output measures from the BMQ [Dryness, Moistness] and a secondary objective measure, Salivary Flow rate [Sflow]. During V4, results show that there were no statistically significant effects for either the Dryness or Moistness measure, over time, for the two tablets. Results also show a statistically significant (p=0.0064) objective increase in salivary flow rate over Time for both tablets during visit 4; but there were no statistically significant differences between the tablets.

V2 vs V5 Baseline

Results from the study indicate that, compared to individuals' baseline subjective and objective measures, participants perceive a statistically significant increase in moistness as well as a statistically significant increase in salivary flow rate. Results also show a marginal, but not statistically significant decrease in the perception of mouth dryness.

Other Results:

Perceptions of freshness [Item #1: Fresh] and staleness [Item #3: Stale] were not significantly different for the two tablets, nor for any time period, for either V3 or V4. Halitosis measures were also examined for V3 and V4, for within-subjects differences and between-groups differences. No statistically significant differences were found for these outcome measures.

Conclusions

1. There is a significant improvement in objective flow rates over the 60 minute period at both V3 (pre-crossover) and V4 (post-crossover) following both tablets.
2. There is a marginal improvement for Tablet 1 on subjective dryness compared to Tablet 2 over the 60 minute time period at V3.
3. There is a significant improvement in primary subjective flow rates over the 60 minute period at V3 (pre-crossover) for both tablets.
4. There is a significant sustained effect observed in baseline primary subjective measures and objective unstimulated salivary flow rates following the 3 week study period (i.e., V2 to V5) for both tablets.

Example 3

Comparison of Mucoadhesive Tablets with and without Active Agents

Materials and Methods

OraMoist™: lubricating agents (carbomer homopolymer and triglycerides), gustatory/flavoring agents (lemon flavor and citric acid), and antimicrobial agents/enzymes (glucose oxidase, lysozyme, and lactoferrin);

Plain tablets: OraMoist™ minus the sweetener, enzymes, and lubricating agent.

Subjects were randomized in a double-blinded fashion into one of the two disc groups. Both discs were identically packaged and coded with a link to a randomization list, and un-blinding took place after the study was completed. Investigators and subjects were blinded to this process.

Subjects underwent both V3 baseline objective and subjective measurements of mouth dryness, and then were instructed about how to place the disc on the hard palate. Subjective and objective measurements were then taken both at 5 and 60 minutes after disc application. Measurements of whole unstimulated salivary flow rates (mL/min) were taken as per the technique described by Navasesh (Navasesh, et al., J. Amer. Dental Assoc. 2008; 139 Suppl:35S-40S).

Results

Figure 2:
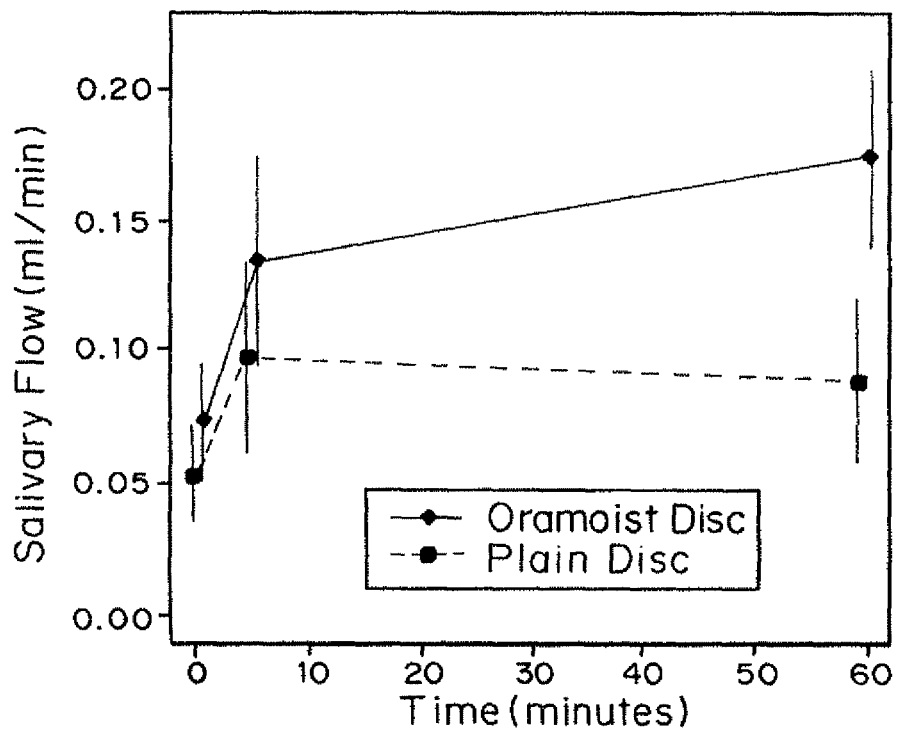
FIG. 2 is a graph of salivary flow (ml/min) over time in minutes comparing the Oramoist disk (diamonds) with a plain disk (square).

Results for VAS score and Salivary flow are shown in FIGS. 1 and 2. The results demonstrate superior results over time for the tablets with actives as compared to mucoadhesive materials only.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A double layer bioadhesive sticker tablet for treating or ameliorating the effects of xerostomia in a patient comprising:
 a bioadhesive layer comprising
  (a) a pharmaceutically acceptable bioadhesive carrier, and
  (b) a non-lipid lubricant selected from the group consisting of polymers of acrylic acid crosslinked with allyl sucrose or allyl pentaerythritol, copolymers of acrylic acid and $C_{10}$-$C_{30}$ alkyl acrylate crosslinked with allyl pentaerythritol, polyethylene glycol having a molecular weight of between about 400 and about 1,000,000 daltons, glycerol, polypropylene glycol, polyvinyl alcohol, polyvinyl pyrrolidone, sodium benzoate, leucine, magnesium stearate, sodium lauryl sulfate, and sodium lauryl sulfoacetate, wherein the non-lipid lubricant is present in an amount from about 10% to about 50% by weight;
 wherein the tablet, upon application to a mucosal surface, adheres to the mucosal tissue for at least 15 minutes;
 wherein the tablet does not completely dissolve prior to about 15 minutes following application to a mucosal surface;
 wherein the tablet does not contain a sialogogic agent, a lipid, or combinations thereof, and
 wherein salivary flow is increased about 30 minutes following administration.

2. The tablet of claim 1, wherein the tablet dissolves following application to the mucosal surface over a period of time from about 15 minutes to about eight hours.

3. The tablet of claim 1, further comprising a flavoring agent, a binder, a buffering agent, or combinations thereof.

4. The tablet of claim 1, wherein the lubricant is present in a therapeutically effective amount to lubricate the mouth following administration.

5. The tablet of claim 4, wherein the lubricant is polyvinylpyrrolidone.

6. The tablet of claim 1, wherein the bioadhesive carrier is present in at least five percent by weight.

7. The tablet of claim 6, wherein the bioadhesive carrier comprises a material selected from the group consisting of copolymers of acrylic or methacrylic acid; esterified polyacrylic acid polymers; maleic acid copolymers; polysaccharides; hydrocolloid gels prepared from polysaccharides extracted from Fronia elephantum, Sapindus trifoliatus, Kunjac, and the cashew tree; cellulose; cellulose derivatives; and combinations thereof.

8. The tablet of claim 7, wherein the bioadhesive carrier comprises a polyacrylic acid polymer crosslinked with a polyalkenyl polyether and hydroxypropyl cellulose.

9. The tablet of claim 1 having a mass of from about 50 mg to about 1000 mg.

10. The tablet of claim 1 having a surface area from about 0.4 $cm^2$ to about 30 $cm^2$ or has a diameter of up to three cm.

11. A method for treating or ameliorating the effects of xerostomia in a patient, comprising:
 administering on the buccal or oral mucosa of the mouth of the patient the double layer bioadhesive sticker tablet of claim 1.

12. The method of claim 11, wherein the tablet is placed on the palate or the cheek.

13. The method of claim 11, wherein the tablet adheres to the buccal or oral mucosa for between about 15 minutes and about eight hours.

14. The method of claim 11, wherein the tablet dissolves following application to the mucosal surface over a period of time ranging from about 15 minutes to about eight hours.

15. The method of claim 11, wherein the lubricant is selected from the group consisting of polyvinyl pyrrolidone, magnesium stearate, and polymers of acrylic acid crosslinked with allyl sucrose or allyl pentaerythritol, and copolymers of acrylic acid and $C_{10}$-$C_{30}$ alkyl acrylate crosslinked with allyl.

16. The tablet of claim 1, wherein the non-lipid lubricant comprises magnesium stearate.

17. The tablet of claim 1, wherein the non-lipid lubricant is present in an amount from about 20% to about 40% by weight.

18. The tablet of claim 1, wherein the non-lipid lubricant is present in an amount from of about 37% by weight.

* * * * *

UNITED STATES PATENT AND TRADEMARK OFFICE
CERTIFICATE OF CORRECTION

PATENT NO.         : 9,161,909 B2
APPLICATION NO.    : 12/757508
DATED              : October 20, 2015
INVENTOR(S)        : Abraham J. Domb, Benny Brama and Boaz Mizrahi Page 1 of 1

It is certified that error appears in the above-identified patent and that said Letters Patent is hereby corrected as shown below:

Specification,
Column 2, line 35, replace "xersotomia" with --xerostomia--.
Column 2, line 38, replace "There has been some success clinical reported" with --There has been some clinical success reported--.
Column 4, lines 44-45, replace "administration" with --administration.--.
Column 5, line 30, replace "of the of the" with --of the--.
Column 5, line 67 to column 6, line 1, replace "hydroxypropylm-ethyl" with --hydroxypropyl-methyl--.
Column 6, line 2, replace "non-cross linked" with --non-cross-linked--.
Column 6, line 38, replace "fatty-acids" with --fatty acids--.
Column 9, lines 3-4, replace "typically accounts for about 90% of the mass, and comprises mostly sugar alcohols, but includes" with --typically account for about 90% of the mass, and comprise mostly sugar alcohols, but include--.
Column 9, line 67, replace "cheek" with --cheek.--.
Column 10, line 21, replace "places" with --placed--.
Column 13, line 20, replace "affect" with --effect--.
Column 14, line 24, replace "palate" with --tablet--.
Column 16, line 20, replace "separately" with --separately.--.
Claims,
Claim 10, column 20, line 23, replace "has" with --having--.
Claim 18, column 20, line 49, replace "in an amount from of" with --in an amount of from--.

Signed and Sealed this
Twenty-second Day of March, 2016

Michelle K. Lee
*Director of the United States Patent and Trademark Office*